United States Patent
Gorek

(10) Patent No.: US 6,638,281 B2
(45) Date of Patent: Oct. 28, 2003

(54) GRAVITY DEPENDENT PEDICLE SCREW TAP HOLE GUIDE

(75) Inventor: Josef E. Gorek, Larkspur, CA (US)

(73) Assignee: SpineCore, Inc., Summit, NJ (US)

( * ) Notice: Subject to any disclaimer, the term of this patent is extended or adjusted under 35 U.S.C. 154(b) by 0 days.

(21) Appl. No.: 10/103,079

(22) Filed: Mar. 21, 2002

(65) Prior Publication Data

US 2003/0181919 A1 Sep. 25, 2003

(51) Int. Cl.$^7$ .................. A61B 17/58; A61B 17/60; A61F 2/00; A61F 2/32; A61F 2/34
(52) U.S. Cl. ............................... 606/96; 606/104
(58) Field of Search .................. 606/86, 96, 99, 606/104

(56) References Cited

U.S. PATENT DOCUMENTS

| | | | | | |
|---|---|---|---|---|---|
| 2,666,430 A | * | 1/1954 | Gispert | ................. | 128/83 |
| 4,164,871 A | * | 8/1979 | Cole et al. | ............. | 73/432 |
| 4,257,411 A | * | 3/1981 | Cho | ................. | 128/92 |
| 4,823,780 A | * | 4/1989 | Odensten et al. | ........ | 128/92 |
| 5,467,532 A | * | 11/1995 | Ames | ................. | 33/334 |
| 6,045,508 A | * | 4/2000 | Hossack et al. | ........ | 600/447 |
| 6,263,984 B1 | * | 7/2001 | Buckman, Sr. | ........ | 175/67 |
| 2002/0095159 A1 | * | 7/2002 | Deloge et al. | ........ | 606/98 |

* cited by examiner

Primary Examiner—Eduardo C. Robert
Assistant Examiner—Anuradha Ramana
(74) Attorney, Agent, or Firm—Joseph P. Errico, Esq.; Timothy J. Bortree, Esq.

(57) ABSTRACT

A gravity dependent pedicle screw tap hole guide comprises a guide shaft maintainable parallel to a drill bit during the drilling of a pedicle screw tap hole; a level indicator associated with a reference direction and responsive to gravity to provide feedback regarding an angular difference between an acting direction of gravity and the reference direction; and a mounting attaching the indicator to the shaft and establishing a positional relationship between the reference direction and the longitudinal axis. Using the guide involves angulating the shaft about its distal end adjacent the base of the superior articular process and the base and middle of the transverse process until the guide indicates that the angular orientation of the longitudinal axis matches the previously determined pedicle axis orientation with respect to the acting direction of gravity, and then drilling the tap hole along a trajectory established by the longitudinal axis of the shaft.

15 Claims, 4 Drawing Sheets

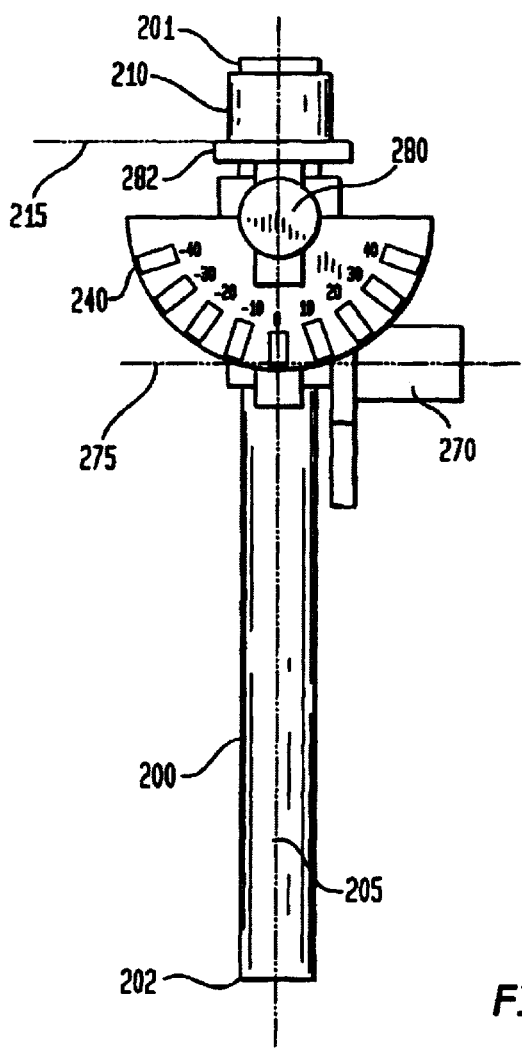
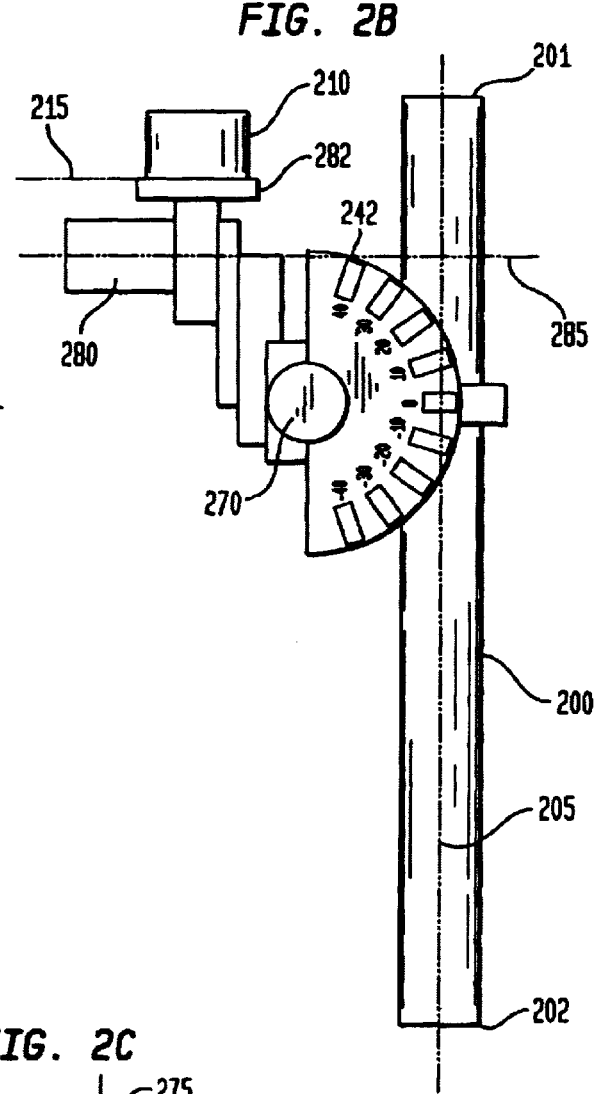
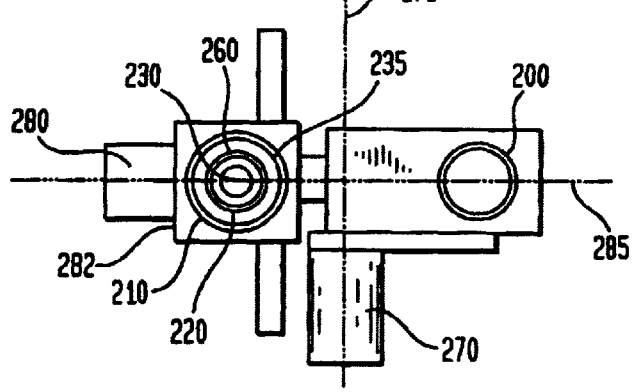
FIG. 2A
FIG. 2B
FIG. 2C

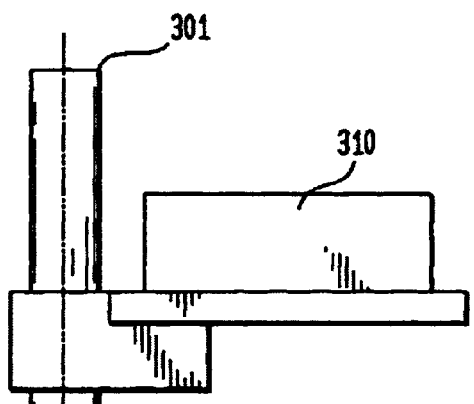
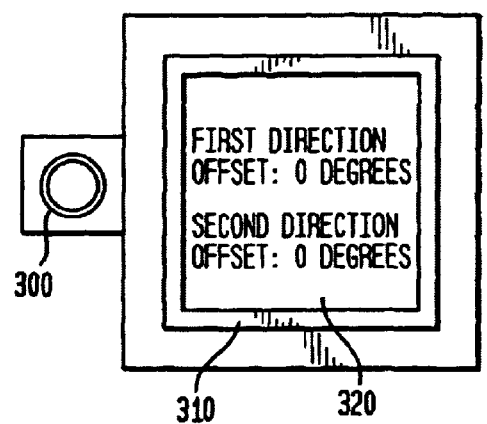
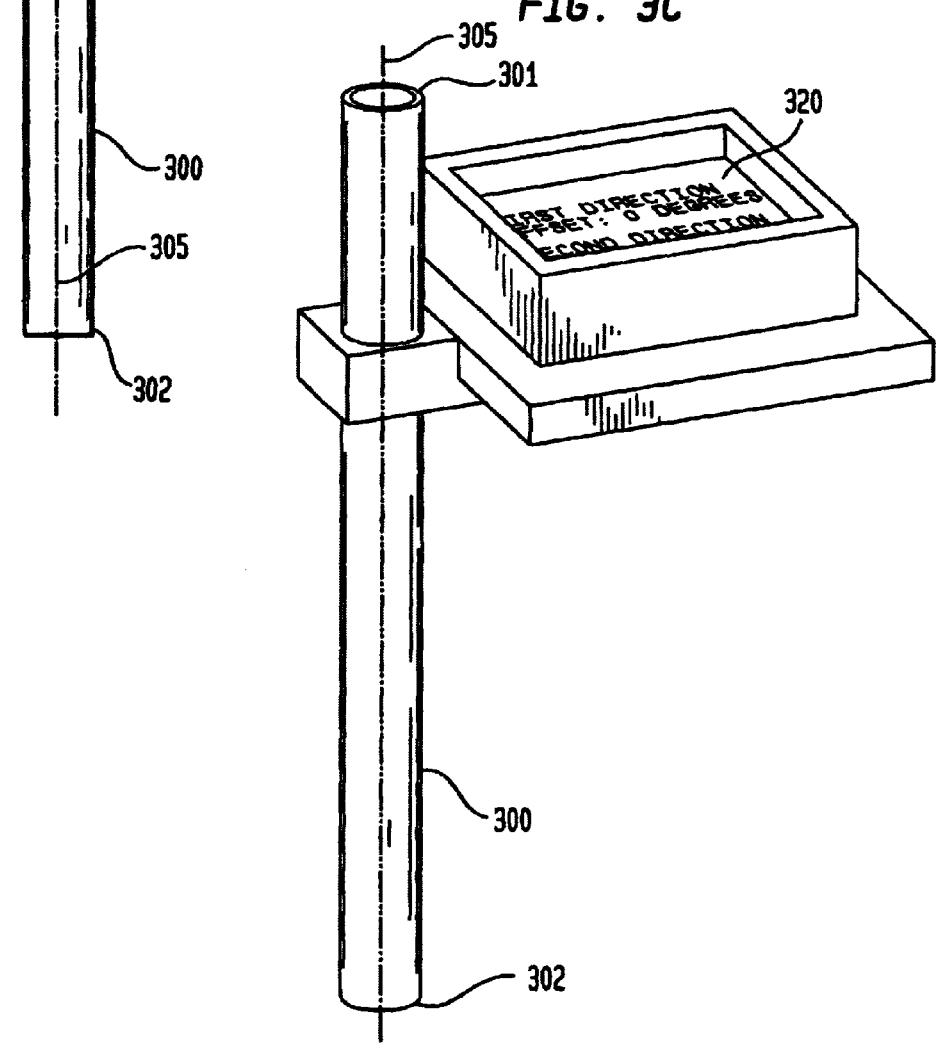

GRAVITY DEPENDENT PEDICLE SCREW TAP HOLE GUIDE

FIELD OF THE INVENTION

This invention relates generally to devices and methods for inserting pedicle screws into the spine, and more specifically to devices and methods for accurately establishing a pedicle screw tap hole drilling trajectory.

BACKGROUND OF THE INVENTION

The bones and connective tissue of an adult human spinal column consist of more than 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic and lumbar spine.

The spinal column of bones is highly complex in that it includes these more than 20 bones coupled to one another, housing and protecting critical elements of the nervous system having innumerable peripheral nerves and circulatory bodies in close proximity. In spite of these complexities, the spine is a highly flexible structure, capable of a high degree of curvature and twist in nearly every direction. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art that achieve this immobilization by implanting artificial assemblies in or on the spinal column. These assemblies may be classified as anterior, posterior, or lateral implants. As the classifications suggest, lateral and anterior assemblies are coupled to the anterior portion of the spine, which is the sequence of vertebral bodies. Posterior implants generally comprise pairs of rods, which are aligned along the axis along which the bones are to be disposed, and which are then attached to the spinal column by either hooks which couple to the lamina or attach to the transverse processes, or by screws which are inserted through the pedicles.

The pedicles are the strongest parts of the vertebrae and therefore provide a secure foundation for the screws to which the rods are to be attached. In order to obtain the most secure anchor for the pedicle screws, it is essential that the screws be threaded in alignment with the pedicle axis and not be allowed to deviate therefrom. Misalignment of the pedicle screws during insertion can cause the screw body or its threads to break through the vertebral cortex and be in danger of striking surrounding nerve roots. A variety of undesirable symptoms can easily arise when the screws make contact with nerves after breaking outside the pedicle cortex, including dropped foot, neurological lesions, sensory deficits, or pain.

Known surgical procedures to avoid misalignment of the pedicle screws involve recognizing landmarks along the spinal column for purposes of locating optimal tap hole entry points, approximating tap hole trajectories, and estimating proper tap hole depth. Some surgeons use a Kocher clamp applied to the vertebral bone for a reference mark and/or view radiographs or other medical images to better understand relative positions of the patient's anatomy. X-ray exposures and/or fluoroscopy can sometimes be used to monitor the advancement of a pedicle screws through the vertebra. Unfortunately, these procedures are subject to surgeon visual approximation errors, and anatomical landmarks are different for each patient. Further, prolonged radiation exposure to a patient is undesirable. U.S. Pat. No. 4,907,577 (Mar. 13, 1990) discloses a jig that is described therein as providing a safe route for drilling pedicle screw tap holes, by identifying a precise location for drilling to prevent deviation from the drilling direction so as to prevent injury during surgery to the nerve root or spinal cord. However, the jig has a variety of moving parts that must be adjusted and monitored simultaneously during the adjustments, making operation of the jig difficult and time consuming. Further, operation of the jig must occur during surgery, as it must be held adjacent the vertebral body to determine the proper adjustment settings. Finally, adjustment of the jig to the proper settings requires precise visual approximation by the surgeon, an activity that should be minimized to ensure that a misaligned trajectory is not established in place of a safe one.

More technologically advanced systems such as the StealthStation™ Treatment Guidance System, the FluoroNav™ Virtual Fluoroscopy System (both available from Medtronic Sofamor Danek), and related systems, seek to overcome the need for surgeons to approximate landmarks, angles, and trajectories, by assisting the surgeons in determining proper tap hole starting points, trajectories, and depths. However, these systems are extremely expensive, require significant training, are cumbersome in operation, are difficult to maintain, and are not cost effective for many hospitals.

U.S. Pat. No. 5,474,558 (Dec. 12, 1995) and 5,196,015 (Mar. 23, 1993) propose a procedure in which a screw opening is started in part of a skeletal region, e.g., a pedicle of a lumbar vertebra, and an electric potential of a certain magnitude is applied to the inner surface of the opening while the patient is observed for nervous reactions such as leg twitching. The opening continues to be formed while the electric potential is applied until a desired hole depth is obtained in the absence of nervous reaction to the potential. The direction in which the screw opening is being formed is changed to a direction other than the last direction, after observing patient reactions to the electric potential when the screw opening was being formed in the last direction. Unfortunately, this procedure is inherently reactive rather than proactive, in that the surgeon becomes aware of the misalignment after the patient exhibits a nervous reaction, and by that time the misaligned hole has been drilled.

Therefore, there is a need for a simple device that eases the difficulties associated with safely placing pedicle screws. Specifically, there is a need for such a device that assists a surgeon in making more accurate the surgeon's assessment of the proper insertion trajectory of the pedicle screw. Further, there is a need for such a device that does not require the surgeon to rely on visual approximations. In addition, there is a need for such a device that proactively determines the desirable drilling trajectory rather than reactively informing the surgeon when an improper trajectory has been used.

SUMMARY OF THE INVENTION

The needs identified above and other needs in the art are achieved by the present invention that provides a gravity dependent pedicle screw tap hole guide and methods of use thereof.

One embodiment of a gravity dependent pedicle screw tap hole guide of the present invention has a shaft with a proximal end, a distal end, a longitudinal axis, and a fluid chamber attached to the shaft. A bubble in the fluid chamber indicates whether or not the chamber is level and/or to what degree it is not level. The translucent wall of the chamber has a reference mark positioned so that that when the bubble is centered under the reference mark, the longitudinal axis of the shaft is parallel to the acting direction of gravity. The wall also has a grid that, when the bubble is not centered under the reference mark, indicates an angular difference (preferably in two perpendicular planes) between the longitudinal axis of the shaft and the acting direction of gravity. Preferably, the longitudinal axis of the shaft extends perpendicular to a plane in which a platform holding the chamber extends. The chamber is preferably a hemispherical enclosure with a central axis that is parallel to the longitudinal axis of the shaft.

In operation of this embodiment, the surgeon first exposes a vertebral bone and applies a Kocher clamp to the spinous process in a vertical position (where the longitudinal axis of the clamp is parallel to the acting direction of gravity) to his best visual approximation. Preferably, the guide of this embodiment is used here to make the vertical placement more accurate, by holding the shaft parallel to the longitudinal axis of the Kocher clamp while manipulating the shaft with the Kocher clamp so that when the bubble is centered under the reference mark, the surgeon knows that the Kocher clamp is in a vertical position.

Next, a lateral radiograph is taken and used to approximate the cephalad-caudad declination of the pedicle of interest and the medial angulation of the pedicle is determined from preoperative transaxial MRI and/or CAT scan images. The surgeon then positions the distal end of the shaft against the exposed vertebral bone in the vicinity of the base of the superior articular process and the base and middle of the transverse process (referred to herein as the "preferred tap hole entry point"), and angulates the shaft until the angular difference between the longitudinal axis of the shaft and the acting direction of gravity matches the determined cephalad-caudad declination (in the cephalad-caudad plane), and the medial angulation (in the medial plane). During this angulation, the surgeon can view the bubble's position relative to the grid lines, to know when and in what direction additional angulational adjustment of the shaft is necessary to bring the shaft to the desired position.

Once the shaft has been placed in the desired position, the surgeon can be confident that drilling into the vertebral bone along the trajectory established by the longitudinal axis of the shaft in the desired position will result in a pedicle screw tap hole that is formed to maximize the stability of a pedicle screw subsequently screwed thereinto. The shaft can be hollow to accommodate a drill bit for this purpose, or, if the shaft is not hollow, the distal end of the drill bit can be placed against the preferred tap hole entry point of the exposed vertebral bone, and the shaft can be held parallel to the longitudinal axis of the drill bit so that the shaft and the drill bit can be angulated in parallel together until the guide indicates the drill bit is at the desired angle.

Another embodiment of a gravity dependent pedicle screw tap hole guide of the present invention also has a shaft with an attached fluid chamber housing a level-indicating bubble that rests under a reference mark when the chamber is level. The chamber is movably attached to the shaft and thereby positionable relative to the shaft. Specifically, the degree of perpendicularity of the longitudinal axis of the shaft relative to a plane defined by the chamber can be varied in at least two planes. In this regard, the movable attachment of the chamber to the shaft is achieved by two rotatable mountings, the first being between the shaft and the second rotatable mounting, and the second being between the first rotatable mounting and the chamber. The first rotatable mounting rotates about an axis extending perpendicular to the longitudinal axis of the shaft, and the second rotatable mounting rotates about an axis extending perpendicular to the plane defined by the chamber. Each of the rotatable mountings can be secured at any position to which it can be rotated. When each rotatable mounting is in its zero position, the plane of the chamber is perpendicular to the longitudinal axis of the shaft and, accordingly, when the enclosure is oriented such that the bubble is under the reference mark, the longitudinal axis of the shaft is parallel to the acting direction of gravity. Marks on the mountings preferably indicate the relative angle of rotation of the rotatable mounting with respect to the zero position, such that if either or both of the rotatable mountings are placed in a rotated position, the user can read the marks to determine the angular difference between the longitudinal axis of the shaft and the plane defined by the chamber when the chamber is oriented so that the bubble is under the circle.

In operation of this embodiment, the surgeon proceeds as indicated above with regard to the first embodiment, but use of this embodiment to make the Kocher clamp vertical placement more accurate is as follows: The rotatable mountings are placed in their respective zero positions, and the shaft is held parallel to the longitudinal axis of the Kocher clamp while being manipulated with the Kocher clamp until the bubble is centered under the reference mark, at which time the surgeon knows that the Kocher clamp is in a vertical position.

After determining the cephalad-caudad declination and medial angulation of the pedicle of interest, the surgeon places the first rotatable mounting into a rotated position at an angular offset matching the cephalad-caudad declination, and places the second rotatable mounting into a rotated position at an angular offset matching the medial angulation. During these rotations, the surgeon can view the marks to ensure that the mountings are rotated to the desired angles. Then, the surgeon positions the distal end of the shaft against the preferred tap hole entry point, and angulates the shaft until the bubble is under the reference mark. The surgeon can then safely drill the tap hole as desired along the trajectory established by the longitudinal axis of the shaft. Again, the shaft can be hollow and/or held in parallel to the drill bit as the drill bit is angulated against the preferred tap hole entry point.

Yet another embodiment of a gravity dependent pedicle screw tap hole guide of the present invention is similar to the first embodiment discussed above, but uses an accelerometer instead of a fluid chamber housing a level-indicating bubble. An accelerometer is known in the art as an electronic device that can determine its angular orientation relative to the acting direction of gravity, and therefore can be used to determine, for any device in fixed relation to the accelerometer, the angular orientation of that device relative to the acting direction of gravity. The accelerometer can be connected to an analog or digital readout presenting the angular orientation of the accelerometer relative to the acting direction of gravity. Preferably, the shaft is attached in fixed relation to the accelerometer such that when the accelerometer indicates that there is no angular difference between the reference direction recognized by the accelerometer and the acting direction of gravity, the longitudinal axis of the shaft is parallel to the acting direction of gravity.

Accordingly, as the shaft is oriented freely in space, the accelerometer indicates the angular difference (preferably in two planes) between the longitudinal axis of the shaft and the acting direction of gravity.

Operation of this embodiment proceeds as indicated with regard to the first embodiment, with the accelerometer (rather than the fluid-containing enclosure in the first embodiment) indicating when the shaft is in the desired position, that is, when the angular difference between the longitudinal axis of the shaft and the acting direction of gravity matches the cephalad-caudad declination (in the cephalad-caudad plane) and medial angulation (in the medial plane) of the pedicle.

Still another embodiment of a gravity dependent pedicle screw tap hole guide of the present invention is similar to that of the second embodiment described above, except that the fluid-containing enclosure of that embodiment is replaced with an accelerometer similar to the accelerometer of the third embodiment described above. Accordingly, when each rotatable mounting is in its zero position, and the accelerometer reads level, the longitudinal axis of the shaft is parallel to the acting direction of gravity. And, accordingly, if either or both of the rotatable mountings are placed in a rotated position, the user can, when the accelerometer is oriented level, read the marks to determine the angular difference between the longitudinal axis of the shaft and the acting direction of gravity.

Operation of this embodiment proceeds as indicated with regard to the second embodiment, with the accelerometer indicating when the accelerometer is oriented level (and thus, if the rotatable mountings have been rotated to match the cephalad-caudad declination and medial angulation of the pedicle, that the shaft is at the desired angulation).

BRIEF DESCRIPTION OF THE DRAWINGS

FIGS. 2*a*–*c* are front, side, and top views of another embodiment of a gravity dependent pedicle screw tap hole guide of the present invention, the guide utilizing a fluid chamber housing a level-indicating bubble and rotatable mountings.

FIGS. 3*a*–*c* are side, top, and perspective views of yet another embodiment of a gravity dependent pedicle screw tap hole guide of the present invention, the guide utilizing an accelerometer.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions that follow are to be understood as illustrative and exemplary of specific structures, aspects and features within the broad scope of the present invention and not as limiting of such broad scope. Like numbers refer to similar features of like elements throughout.

Figure 1A:
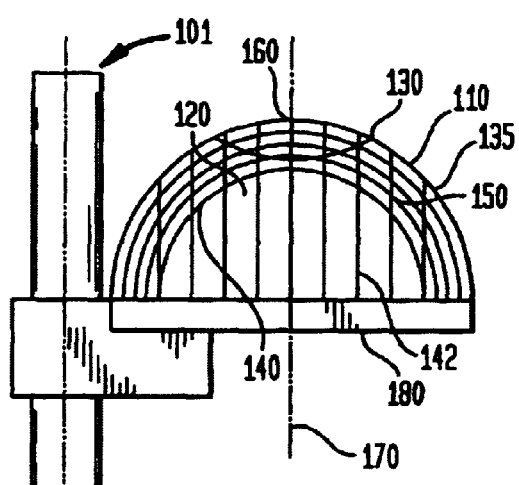
FIGS. 1*a*–*c* are side, top, and perspective views of an embodiment of a gravity dependent pedicle screw tap hole guide of the present invention, the guide utilizing a fluid chamber housing a level-indicating bubble.
Figure 1B:
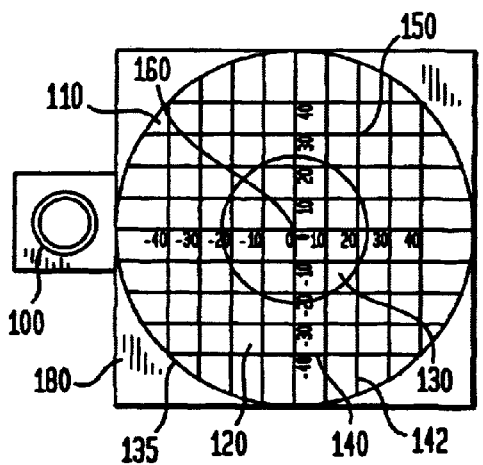
Figure 1C:
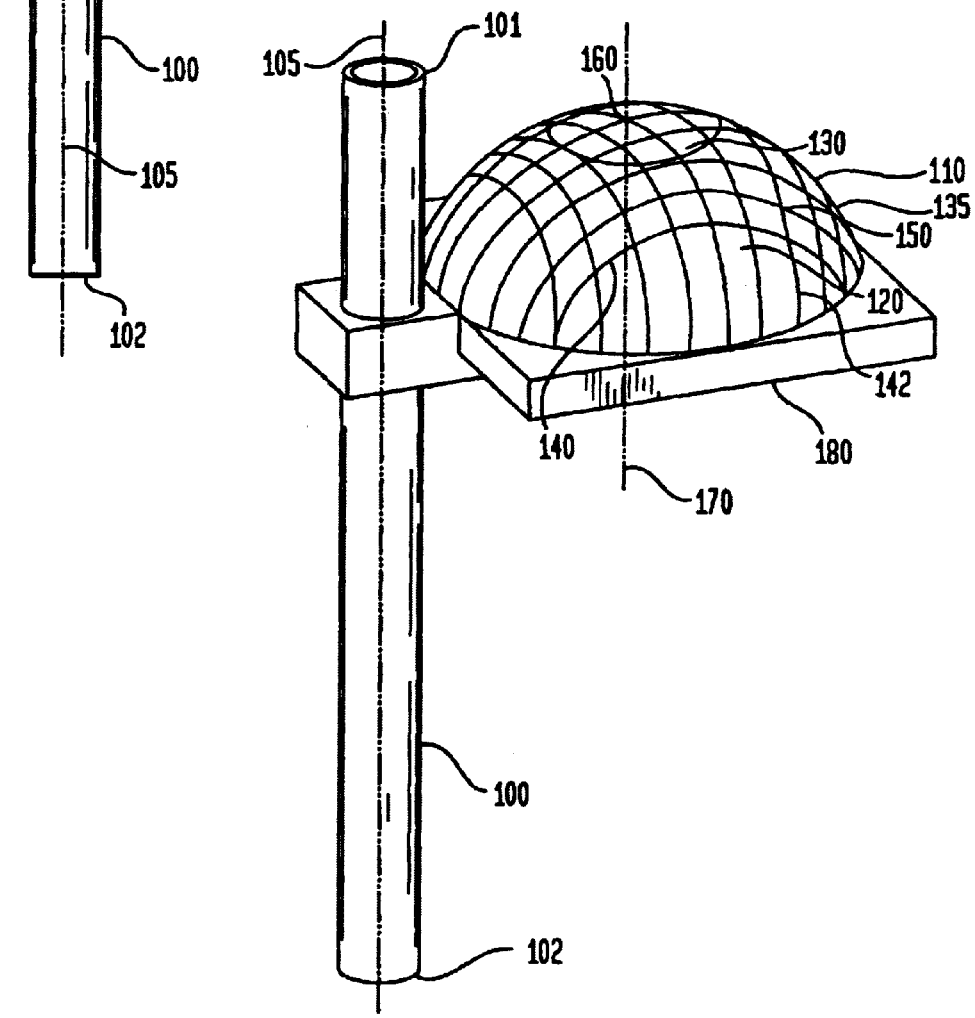

Referring now to FIGS. 1*a*–*c*, an embodiment of a gravity dependent pedicle screw tap hole guide of the present invention is illustrated. The guide in this embodiment has a shaft 100 that has a proximal end 101 and a distal end 102 and a longitudinal axis 105, and a fluid chamber 110 attached to the shaft 100. The fluid chamber 110 is partially filled with fluid 120, and the fluid 120 is contained within the chamber 110, such that a bubble 130 is present in the chamber 110. Because the gas in the bubble 130 is lighter than the fluid in the chamber 110, the bubble 130 floats in the chamber 110, seeking to travel in a direction opposite the acting direction of gravity, but being prevented from leaving the chamber 110 because the chamber 110 is closed.

The chamber 110 has a wall 135 through which the bubble 130 is visible. The wall 135 has a reference mark 160 positioned so that that when the bubble 130 is centered under the reference mark 160, it is indicated that the longitudinal axis 105 of the shaft 100 is parallel to the acting direction of gravity.

Further, the translucent wall 135 has at least one relative mark (grid 150) that can be read to determine the location of the center of the bubble 130 relative to the reference mark 160 when the bubble 130 is not centered under the reference mark 160, the relative mark (grid 150) indicating an angular difference between the longitudinal axis 105 of the shaft 100 and the acting direction of gravity.

Preferably, as shown, the longitudinal axis 105 of the shaft 100 extends in a direction perpendicular to a plane in which a platform 180 laterally attached to the shaft 100 extends. The chamber 110 is preferably a transparent hemispherical enclosure 110 having a central axis 170 (the axis 170 passing through the center top of the hemisphere 110 and being perpendicular to the platform 180) is parallel to the longitudinal axis 105 of the shaft 100.

Also preferably, the outer surface of the enclosure 110 is marked with a guide grid 150 formed by grid lines as shown. Grid lines in a first grid line set 140 are evenly spaced along the curved surface of the enclosure 110 and extend in respective planes parallel to the longitudinal axis 105 of the shaft 100. (Only one grid line of this set is marked 140 merely for clarity in presentation of the figures; the reference numeral 140 applies to the entire set of grid lines). Grid lines in a second grid line set 142 are evenly spaced along the curved surface of the enclosure 110 and extend in respective planes parallel to the longitudinal axis 105 of the shaft 100 but perpendicular to the grid lines in the first set 140. (Only one grid line of this set is marked 142 merely for clarity in presentation of the figures; the reference numeral 142 applies to the entire set of grid lines). The central grid line of each set intersects with the other to define the reference mark 160.

Accordingly, each grid line in the first set 140 indicates (when the bubble 130 is under the line) a respective angular difference between the longitudinal axis 105 of the shaft 100 and the acting direction of gravity in a first plane, and each grid line in the second set 142 indicates (when the bubble is under the line) a respective angular difference between the longitudinal axis 105 of the shaft 100 and the acting direction of gravity in a second plane perpendicular to the first plane. The lines are preferably labeled to assist the surgeon in quantifying the angular difference. In this embodiment, grid lines in the first set 140 are labeled in degrees, in reference to the first plane, −40, −30, −20, −10, 0, 10, 20, 30, 40, respectively. Also in this embodiment, grid lines in the second set 142 are labeled in degrees, in reference to the second plane, −40, −30, −20, −10, 0, 10, 20, 30, 40, respectively. It should be understood that other labeling, with greater or lesser angles, and/or greater or lesser increments, can also be used.

In operation of this embodiment, the surgeon first exposes the vertebral bone into which the pedicle screw is to be placed. Next, the surgeon applies a clamp (e.g., a Kocher clamp) to the spinous process of the exposed vertebral bone, placing the Kocher clamp in a vertical position (parallel to the acting direction of gravity) to his best visual approximation. Preferably, the gravity dependent pedicle screw tap hole guide of this embodiment is used at this point in the procedure to make more accurate the surgeon's vertical placement of the Kocher clamp. That is, the shaft of the guide can be held parallel to the longitudinal axis of the Kocher clamp, manipulated with the Kocher clamp while being maintained in said parallel position, so that when the bubble 130 is centered under the reference mark 160, the surgeon knows that the Kocher clamp is in the vertical position.

Once the Kocher clamp in attached to the spinous process in the vertical position, a lateral radiograph is taken, and the cephalad-caudad declination of the pedicle of interest is determined by the surgeon to his best visual approximation using the longitudinal axis of the Kocher clamp in the radiograph image as the "zero" axis. Also, the medial angulation of the pedicle is determined from preoperative transaxial MRI and/or CAT scan images. Angular measurement devices known in the art can be used to make these angular assessments more accurate. Once the cephalad-caudad declination and the medial angulation have been determined, the surgeon positions the distal end 102 of the shaft 100 against the exposed vertebral bone in the vicinity of the base of the superior articular process and the base and middle of the transverse process (referred to herein as the "preferred tap hole entry point"), and angulates the shaft 100 until the angular difference between the longitudinal axis 105 of the shaft 100 and the acting direction of gravity in the first plane matches the determined cephalad-caudad declination, and the angular difference between the longitudinal axis 105 of the shaft 100 and the acting direction of gravity in the second direction matches the determined medial angulation. (It should be understood that alternatively, the device can be used with the grid lines in the set 140 begin use to match the medial angulation, and the grid lines in the set 142 being used to match the cephalad-caudad declination.) During this angulation, the surgeon can view the position of the bubble 130 under the guide grid 150, and particularly the bubble's position relative to the grid lines, to know when and in what direction additional angulational adjustment of the shaft 100 is necessary to bring the shaft 100 closer to the desired position, and when the shaft 100 has reached the desired position.

Once the shaft 100 has been placed in the desired position, the surgeon can be confident that drilling into the vertebral bone along the trajectory established by the longitudinal axis of the shaft 100 in the desire position will result in a pedicle screw tap hole that is formed to maximize the stability of a pedicle screw subsequently screwed thereinto. That is, the surgeon can be confident that the drilling is unlikely to result in penetration of the distal end of the drill bit to any outer surface of the vertebral bone, and is likely to result in the walls of the tap hole being relatively uniformly thick at any given cross-section. Drilling into the vertebral bone along the trajectory established by the longitudinal axis 105 of the shaft 100 in the desired position can be accomplished in that the shaft 100 can be hollow, as shown, with its internal diameter being sufficient to accommodate a drill bit suitable for drilling the tap hole, and with its length being shorter than the exposed length of the drill bit (the amount of the drill bit protruding from the drill) by an amount sufficient to allow the drill bit to go into the bone to the clinically desired depth before the drill hits the proximal end of the shaft 100. The drill bit can therefore be passed into the shaft 100, and can be rotated therein during the drilling, so that the tap hole is drilled along an extension of the longitudinal axis of the shaft 100 at the desired angle.

Alternatively, the distal end of the drill bit can be placed against the preferred tap hole entry point of the exposed vertebral bone, and the shaft 100 can be held parallel to the longitudinal axis of the drill bit. (This parallel holding can be accomplished, for example, by using suitable attachments or mountings for the shaft against the drill.) The drill bit and the shaft 100 can be angulated together (while being maintained in relative parallel positions) until the angular difference between the longitudinal axis 105 of the shaft 100 and the acting direction of gravity in the first plane matches the determined cephalad-caudad declination, and the angular difference between the longitudinal axis 105 of the shaft 100 and the acting direction of gravity in the second plane matches the determined medial angulation. (It should be understood that alternatively, the device can be used with the grid lines in the set 140 begin use to match the medial angulation, and the grid lines in the set 142 being used to match the cephalad-caudad declination.) During this angulation, the surgeon can view the position of the bubble 130 under the guide grid 150, and particularly the bubble's position relative to the grid lines, to know when and in what direction additional angulational adjustment of the drill bit (and parallel shaft 100) is necessary to bring the drill bit closer to the desired position, and when the drill bit has reached the desired position. Once the drill bit has been placed in the desired position, the surgeon can be confident that drilling into the vertebral bone along the trajectory established the longitudinal axis of the drill bit in the desired position will result in a pedicle screw tap hole that is formed to maximize the stability of a pedicle screw subsequently screwed thereinto.

Referring now to FIGS. 2a–c, another embodiment of a gravity dependent pedicle screw tap hole guide of the present invention is illustrated. The guide in this embodiment has a shaft 200 that has proximal end 201 and a distal end 202 and a longitudinal axis 205, and a fluid chamber 210 attached to the shaft 200. The fluid chamber 210 is partially filled with fluid 220, and the fluid 220 is contained within the chamber 210, such that a bubble 230 is present in the chamber 210. Because the gas in the bubble 230 is lighter than the fluid in the chamber 210, the bubble 230 floats in the chamber 210, seeking to travel in a direction opposite the acting direction of gravity, but being prevented from leaving the chamber 210 because the chamber 210 is closed. Preferably, as shown, the chamber 210 defines a plane 215 that is perpendicular to the acting direction of gravity when the chamber 210 is held level. The chamber 210 has a translucent wall 235 through which the bubble 230 is visible. The translucent wall 235 has a reference mark 260 positioned so that that when the chamber 210 is held level, the bubble 230 is centered under the reference mark 260. The chamber 210 is movably attached to the shaft 200 and thereby positionable relative to the shaft 200. Specifically, the degree of perpendicularity of the longitudinal axis 205 of the shaft 200 relative to the plane 215 defined by the chamber 210 can varied in at least two planes.

Preferably, as shown, a platform 282 is laterally attached to the shaft 200. The chamber 210 is a transparent cylindrical enclosure 210 mounted on the platform 282, the bottom surface 215 of the chamber 210 defining the plane 215. Also preferably, an upper surface 235 of the enclosure is centrally marked with a circle 260. When the chamber 210 is oriented so that the bottom surface 215 is held level, the bubble 230 is under the circle 260.

Also preferably, the movable attachment of the chamber 210 to the shaft 200 is achieved by two rotatable mountings 270, 280 between the chamber 210 and the shaft 200. The first rotatable mounting 270 is between the shaft 200 and the second rotatable mounting 280. The second rotatable 280 mounting is between the first rotatable mounting 270 and the chamber 210. The first rotatable mounting 270 rotates about an axis 275 extending perpendicular to the longitudinal axis 205 of the shaft 200, and the second rotatable mounting 280 rotates about an axis 285 extending perpendicular to the plane 215 defined by the chamber 210. Each of the rotatable mountings 270, 280 can be secured at any position to which it can be rotated. In this embodiment, the securing is accomplished in each rotatable mounting by a set screw that when loose, permits rotation, and when tight, prevents rotation by pressing the relatively moving surfaces of the rotatable mounting against one another. Alternative or additional securing mechanisms can be provided within the scope of the present invention.

Also preferably, the angles of rotation that can be achieved by the rotatable mountings are indicated by two sets 240, 242 of angle marks associated respectively with each rotatable mounting 270, 280. Each set has a zero mark, each zero mark indicating a zero position into which the associated rotatable mounting can be placed. When each rotatable mounting 270, 280 is in its zero position, the plane 215 of the enclosure 210 is perpendicular to the longitudinal axis 205 of the shaft 200 and, accordingly, when the enclosure 210 is oriented such that the bubble 230 is under the circle 260, the longitudinal axis 205 of the shaft 200 is parallel to the acting direction of gravity.

Additional marks in the set preferably indicate the relative angle of rotation of the rotatable mounting with respect to this zero position, such that if either or both of the rotatable mountings are placed in a rotated position, the user can read the marks to determine the angular difference between the longitudinal axis 205 of the shaft 200 and the plane 215 when the enclosure 210 is oriented so that the bubble 230 is under the circle 260. Preferably, each set marks 10 degree increments, e.g., −40, −30, −20, −10, 0, 10, 20, 30, 40, with the first rotatable mounting marks indicating the angular difference in a first plane, and the second rotatable mounting marks indicating the angular offset in a second plane parallel to the first plane. It should be understood that other labeling, with greater or lesser angles, and greater or lesser increments, can also be used.

In operation of this embodiment, the surgeon proceeds as indicated above with regard to the first embodiment, applying a Kocher clamp in a vertical position to the spinous process of the vertebral bone into which the pedicle screw is to be placed. The surgeon can again use his best visual approximation to apply the Kocher clamp vertically, or can preferably use the gravity dependent pedicle screw tap hole guide of this embodiment to make the placement more accurate. That is, the rotatable mountings 270, 280 of the guide can be placed in their respective zero positions, so that the plane 215 of the enclosure 210 is perpendicular to the longitudinal axis 205 of the shaft 200, and the shaft 200 can then be held parallel to the longitudinal axis of the Kocher clamp, and manipulated with the Kocher clamp while being maintained in said parallel position similar to the use of the first embodiment discussed above, so that when the bubble 230 is centered under the circle 260, the surgeon knows that the Kocher clamp is in a vertical position.

Next, a lateral radiograph is taken and used to approximate the cephalad-caudad declination of the pedicle of interest, and the medial angulation of the pedicle is determined from preoperative transaxial MRI and/or CAT scan images. The surgeon then places the first rotatable mounting 270 into a rotated position at an angular orientation matching the cephalad-caudad declination, and places the second rotatable mounting 280 into a rotated position at an angular orientation matching the medial angulation. During these rotations, the surgeon can view the rotatable mounting marks 240, 242 to ensure that the mountings 270, 280 are rotated to the desired angles.

Then, the surgeon positions the distal end 202 of the shaft 200 against the preferred tap hole entry point of the exposed vertebral bone, and angulates the shaft 200 until the bubble 230 is under the circle 260. When the bubble 230 is under the circle 260, this indicates to the surgeon that the angulation of the shaft 200 matches the angulation of the pedicle with respect to the vertical.

Once the shaft 200 has been placed in the desired position, the surgeon can be confident that drilling into the vertebral bone along the trajectory established by the longitudinal axis 205 of the shaft 200 in the desired position will result in a pedicle screw tap hole that is formed to maximize the stability of a pedicle screw subsequently screwed thereinto. Drilling into the vertebral bone along an extension of the longitudinal axis 205 of the shaft 200 can be accomplished in that the shaft 200 can be hollow, as discussed with regard to the first embodiment, and the drill bit passed into and rotated in the shaft 200 during the drilling. Alternatively, also as discussed with regard to the first embodiment, if a hollow shaft is not used, the shaft 200 can be held parallel to the longitudinal axis of the drill bit, and the drill bit and the shaft 200 can be angulated together (while being maintained in relative parallel positions) until the bubble 230 is under the circle 260. When the bubble 230 is under the circle 260, this indicates to the surgeon that the angular orientation of the shaft 200 (and therefore the angular orientation of the drill bit) matches the angular orientation of the pedicle with respect to the vertical.

Referring now to FIGS. 3a–c, yet another embodiment of a gravity dependent pedicle screw tap hole guide of the present invention is illustrated. The guide in this embodiment has a shaft 300 that has a proximal end 301 and a distal end 302 and a longitudinal axis 305, and an accelerometer 310 attached to the shaft 300. The accelerometer 310 is an electronic device that can determine its angular orientation relative to the acting direction of gravity, and therefore can be used to determine, for any device in fixed relation to the accelerometer 310, the angular orientation of that device relative to the acting direction of gravity. Although a variety of accelerometers exist and can be used with the present invention, one example of an accelerometer that can be used with the present invention has as its central functional mechanism a computer chip that determines the angular orientation of a reference direction relative to the acting direction of gravity, and further can be connected to other electronic devices to provide relevant data in that regard to such devices. A suitable accelerometer is sold by Analog Devices, Inc. (Norwood, Mass.) as product number ADXL202. Accordingly, and preferably as shown, an analog or digital readout 320 in communication with the accelerometer 310 is viewable to provide the angular orientation of the accelerometer 310 relative to the acting direction of gravity.

Preferably, as shown, the shaft 300 is attached in fixed relation to the accelerometer 310 such that when the accelerometer 310 indicates that there is no angular difference between the reference direction recognized by the accelerometer 310 and the acting direction of gravity, the longitudinal axis 305 of the shaft 300 is parallel to the acting direction of gravity. Accordingly, as the shaft 300 is oriented freely in space, the accelerometer 310 indicates the angular difference (preferably in two dimensions) between the longitudinal axis 305 of the shaft 300 and the acting direction of gravity.

Operation of this embodiment proceeds as indicated with regard to the first embodiment, with the accelerometer 310 (rather than the fluid-containing enclosure of the first embodiment) indicating when the shaft 300 is in the desired position, that is, when the angular difference between the longitudinal axis of the shaft 300 and the acting direction of gravity matches the cephalad-caudad declination (in the first plane) and medial angulation (in the second plane) of the pedicle.

Figure 4A:
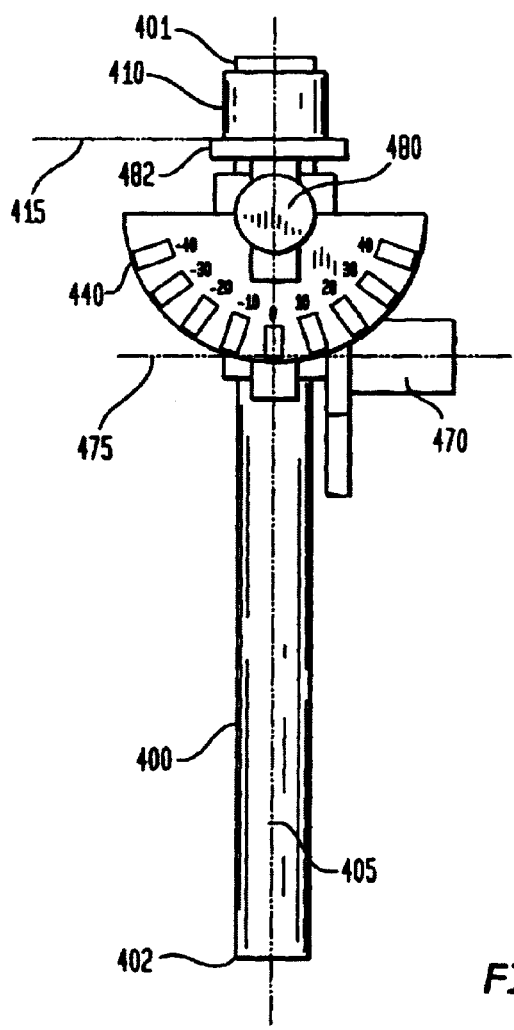
FIGS. 4*a*–*c* are front, side, and top views of still another embodiment of a gravity dependent pedicle screw tap hole guide of the present invention, the guide utilizing an accelerometer and rotatable mountings.
Figure 4B:
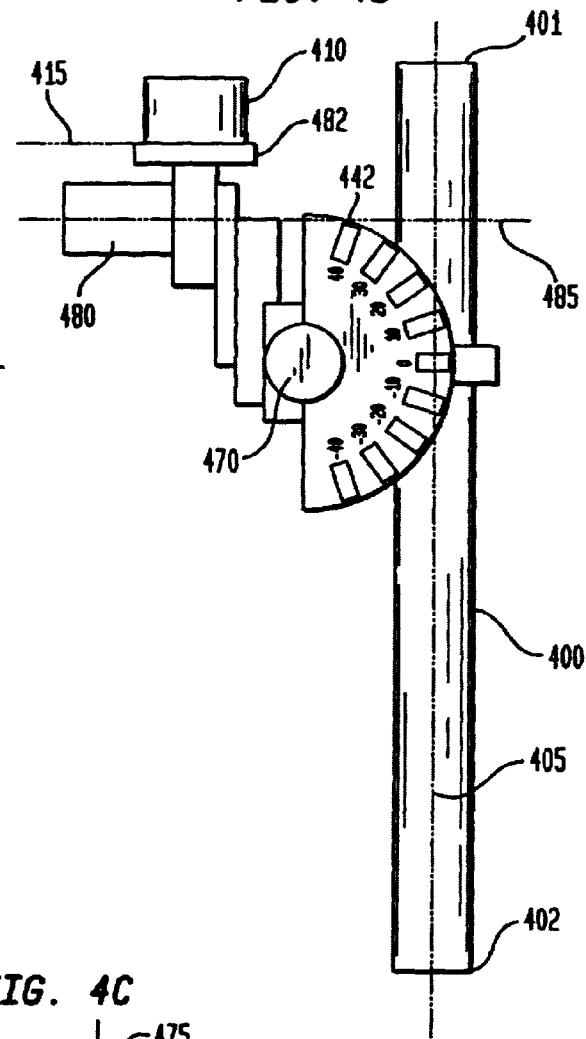
Figure 4C:
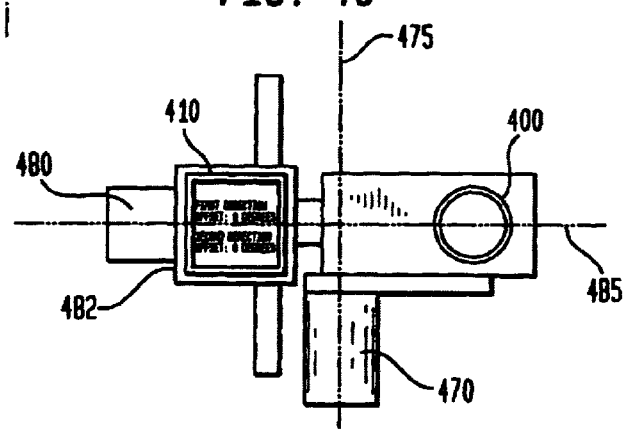

Referring now to FIGS. 4*a*–*c*, still another embodiment of a gravity dependent pedicle screw tap hole guide of the present invention is illustrated. The guide in this embodiment is similar to that of the second embodiment described above, except that the fluid-containing enclosure 210 of that embodiment is replaced with an accelerometer 410 similar to the accelerometer 310 described in the third embodiment described above. Elements in this fourth embodiment that are similar to those in the second embodiment are referenced with like numbers, but in the four hundreds rather than the two hundreds. Accordingly, when each rotatable mounting 470, 480 is in its zero position, and the accelerometer 410 reads level, the longitudinal axis 405 of the shaft 400 is parallel to the acting direction of gravity. And, accordingly, if either or both of the rotatable mountings are placed in a rotated position, the user can read the marks in the mark sets 440, 442 to determine the angular difference between the longitudinal axis 405 of the shaft 400 and the acting direction of gravity when the accelerometer 410 is oriented level.

Operation of this embodiment proceeds as indicated with regard to the second embodiment, with the accelerometer 410 indicating when the accelerometer 410 is oriented level (and thus, if the rotatable mountings 470, 480 have been rotated to match the cephalad-caudad declination and medial angulation of the pedicle, that the shaft 400 is at the desired angulation).

While there has been described and illustrated specific embodiments of an intervertebral spacer device, it will be apparent to those skilled in the art that variations and modifications are possible without deviating from the broad spirit and principle of the present invention. The invention, therefore, shall not be limited to the specific embodiments discussed herein.

What is claimed is:

1. A gravity dependent pedicle screw tap hole guide, comprising:
   a guide shaft having a proximal end, a distal end, and a longitudinal axis, the guide shaft being maintainable parallel to a drill bit during the drilling of a pedicle screw tap hole with the drill bit;
   a level indicator associated with a reference direction and being responsive to gravity to provide feedback regarding an angular difference between an acting direction of gravity and the reference direction; and
   a mounting by which the level indicator is attached to the guide shaft, the mounting establishing a positional relationship between the reference direction and the longitudinal axis of the guide shaft;
   wherein the mounting is adjustable such that the longitudinal axis of the guide shaft is angulatable with respect to the reference direction.

2. The gravity dependent pedicle screw tap hole guide of claim 1, wherein the mounting has at least one indicator that is viewable to determine an angular difference between the longitudinal axis of the guide shaft and the reference direction.

3. The gravity dependent pedicle screw tap hole guide of claim 1, wherein the mounting comprises at least one rotational mounting between the guide shaft and the level indicator, the rotational mounting being engageable and disengageable at a plurality of positions including a parallel position and a plurality of rotated positions, the parallel position being a position at which the longitudinal axis of the guide shaft is parallel to the reference direction, each of the rotated positions being a respective position at which the longitudinal axis of the guide shaft is rotated with respect to the reference direction.

4. The gravity dependent pedicle screw tap hole guide of claim 3, wherein the mounting comprises first and second rotational mountings between the guide shaft and the level indicator, the first rotational mounting providing rotation of the longitudinal axis of the guide shaft relative to the reference direction in a first plane, the second rotational mounting providing rotation of the longitudinal axis of the guide shaft relative to the reference direction in a second plane, the second plane being perpendicular to the first plane, such that the parallel position of the first rotational mounting is a position at which the longitudinal axis of the guide shaft is parallel to the reference direction in the first plane, and the parallel position of the second rotational mounting is a position at which the longitudinal axis of the guide shaft is parallel to the reference direction in the second plane, each of the rotated positions of the first rotational mounting being a respective position at which the longitudinal axis of the guide shaft is rotated with respect to the reference direction in the first plane, and each of the rotated positions of the second rotational mounting being a respective position at which the longitudinal axis of the guide shaft is rotated with respect to the reference direction in the second plane.

5. The gravity dependent pedicle screw tap hole guide of claim 4, wherein each of the first and second rotational mountings has angle markers associated therewith that are viewable to determine an angular difference between the longitudinal axis of the guide shaft and the reference direction.

6. The gravity dependent pedicle screw tap hole guide of claim 1, wherein the level indicator comprises a fluid chamber that is partially filled with fluid such that a gas bubble is free to move in the fluid chamber through a plurality of positions including a position at which the reference direction is parallel to the acting direction of gravity and a plurality of positions at which the reference direction is angulated with respect to the acting direction of gravity, the fluid chamber having a wall through which the gas bubble is visible, the wall having a reference mark indicating the parallel position.

7. The gravity dependent pedicle screw tap hole guide of claim 6, wherein the fluid chamber comprises an enclosure having a convex surface and having a central axis parallel to the reference direction.

8. The gravity dependent pedicle screw tap hole guide of claim 6, wherein the enclosure has a plurality of relative marks indicating the angulated positions.

9. The gravity dependent pedicle screw tap hole guide of claim 8, wherein the wall comprises a grid establishing the reference mark and the relative marks.

10. The gravity dependent pedicle screw tap hole guide of claim 1, wherein the level indicator comprises an accelerometer.

11. The gravity dependent pedicle screw tap hole guide of claim 10, wherein the level indicator further comprises a readout adapted to indicate the angular difference.

12. A gravity dependent pedicle screw tap hole guide, comprising:

a guide shaft having a proximal end, a distal end, and a longitudinal axis, the guide shaft being maintainable parallel to a drill bit during the drilling of a pedicle screw tap hole with the drill bit;

a level indicator associated with a reference direction and being responsive to gravity to provide feedback regarding an angular difference between an acting direction of gravity and the reference direction; and a mounting by which the level indicator is attached to the guide shaft, the mounting establishing a positional relationship between the reference direction and the longitudinal axis of the guide shaft;

wherein the level indicator comprises a fluid chamber that is partially filled with fluid such that a gas bubble is free to move in the fluid chamber through a plurality of positions including a position at which the reference direction is parallel to the acting direction of gravity and a plurality of positions at which the reference direction is angulated with respect to the acting direction of gravity, the fluid chamber having a wall through which the gas bubble is visible, the wall having a reference mark indicating the parallel position.

13. The gravity dependent pedicle screw tap hole guide of claim 12, wherein the fluid chamber comprises an enclosure having a convex surface and having a central axis parallel to tie reference direction.

14. The gravity dependent pedicle screw tap hole guide of claim 12, wherein the enclosure has a plurality of relative marks indicating the angulated positions.

15. The gravity dependent pedicle screw tap hole guide of claim 14, wherein the wall comprises a grid establishing the reference mark and the relative marks.

\* \* \* \* \*